(12) United States Patent
Pierce et al.

(10) Patent No.: US 7,399,789 B2
(45) Date of Patent: *Jul. 15, 2008

(54) BONE TARGETING COMPOUNDS FOR DELIVERING AGENTS TO BONE FOR INTERACTION THEREWITH

(75) Inventors: William M. Pierce, Louisville, KY (US); Leonard C. Waite, Corydon, IN (US); K. Grant Taylor, Louisville, KY (US)

(73) Assignee: University of Louisville Research Foundation, Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/674,753

(22) Filed: Feb. 14, 2007

(65) Prior Publication Data

US 2007/0161710 A1      Jul. 12, 2007

Related U.S. Application Data

(62) Division of application No. 11/021,661, filed on Dec. 22, 2004, now Pat. No. 7,196,220.

(60) Provisional application No. 60/532,342, filed on Dec. 24, 2003.

(51) Int. Cl.
*A61K 31/165* (2006.01)

(52) U.S. Cl. .................. 514/619; 514/568; 514/539

(58) Field of Classification Search ........... 514/619, 514/568, 539; 564/167; 560/45, 103; 562/452
See application file for complete search history.

(56) References Cited

U.S. PATENT DOCUMENTS

| | | | |
|---|---|---|---|
| 5,055,480 A | 10/1991 | Pierce et al. | |
| 5,059,613 A | 10/1991 | Pierce et al. | |
| 5,242,937 A | 9/1993 | Pierce et al. | |
| 5,641,762 A | 6/1997 | Pierce et al. | |
| 7,196,220 B2 * | 3/2007 | Pierce et al. | 564/167 |

FOREIGN PATENT DOCUMENTS

| WO | WO 00/66613 | 9/2000 |
|---|---|---|
| WO | WO 02/55518 | 7/2002 |

OTHER PUBLICATIONS

D.R. Barton, et al., "Experiments of the Synthesis of Tetracycline Part VI: Oxidation and Reduction of Potential Ring A Precursors"; Journal of Chemical Society (C); 1971; 12; pp. 2204-2215.
Beilstein Institut; Chem. Pharm. Bull; 1958; vol. 6; pp. 648-652.
Bretschneider, et al.; Monatshefte Fuer Chemie; 1957; 88; pp. 652-662.
Semenitz, et al.; Antibacterial activity of some 4-substituted derivatives of 1, 3-dihydroxy-2-naphthoic acid; Zeitschrift Fuer Immitaetsforschung Und Experimentelle Therapie; 1961; 115; pp. 466-471.
Nagai, et al.; Preparation of aminodihydroxybenzoic acids; Nov. 8, 2002; Mitsui Chemicals Inc; abstract.
Fieser, et al.; Naphthoquinone antimalarials. X. Miscellaneous compounds with oxygen, halogen, or nitrogen in the side chain; 194; Journal of The Americal Chemical Society; 70; pp. 3206-3211.
Brain, et al.; Derivatives of 6-aminopenicillanic acid. IV. Analogs of 2, 6-dimethoxyphenylpenicillin in the naphthalene and quinoline series; 1963, Journal of Chemical Society; pp. 491-497.
Bobeldijk, et al.; A simple and high-yield synthesis of (S)-BZM, (R)-BZM and (S)-IBZM for the preparation of (S)-123I-IBZM; 1990; Journal of Labelled Compounds and Radiopharmaceuticals; pp. 1247-1256.
Branchini, et al.; Some derivatives of p-orsellinic acid; 1958; Annali Di Chimica (Rome Italy); 48; pp. 819-825.

* cited by examiner

*Primary Examiner*—Shailendra Kumar
(74) *Attorney, Agent, or Firm*—Stites & Harbison PLLC; James Daly, IV; Mandy Wilson Decker

(57) ABSTRACT

The present invention relates to compounds of the formula

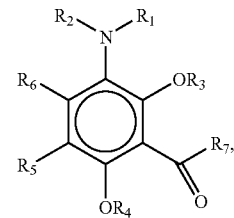

or pharmaceutically acceptable salts thereof, useful for delivering agents having the capacity to diagnose, treat or prevent bone injury or disease to the bone for interaction therewith.

24 Claims, 1 Drawing Sheet

BONE TARGETING COMPOUNDS FOR DELIVERING AGENTS TO BONE FOR INTERACTION THEREWITH

CROSS-REFERENCE TO RELATED APPLICATIONS

This application is a divisional of U.S. patent application Ser. No. 11/021,661 filed Dec. 22, 2004 now U.S. Pat. No. 7,196,220, which claims priority from U.S. Provisional Application Ser. No. 60/532,342 filed Dec. 24, 2003. The entire disclosures contained in U.S. Provisional Application Ser. No. 60/532,342 and U.S. application Ser. No. 11/021,661 are incorporated herein by this reference.

BACKGROUND OF THE INVENTION

The present application relates to compounds useful for delivering agents to bone for treatment of bone injury, bone metabolic disorders, prophylaxis or diagnosis thereof.

Bone is a dynamic tissue, consisting of cells in a protein matrix, upon which is superimposed a crystalline structure of various calcium salts. Bone injury can occur in a variety of manners, for example, a bone fracture, can be caused by excessive force being exerted onto the bone, and bone degeneration can be caused by a relative excess of bone resorption as occurs, for example, with osteoporosis. Regardless of the type of bone injury, it can create substantial problems because bone is the primary support for the body of an animal.

In addition to serving as a rigid support for the body of an animal, bone is an organ which responds to various agents, including hormones, some of which have the ability to increase bone formation or inhibit bone resorption. However, many agents having the capacity to treat or prevent bone injury or metabolic disorders based on their ability to promote bone formation or inhibit bone resorption cannot be effectively used because they lack any bone specificity.

Thus, there remains a need in the art for compounds and methods for imparting bone specificity to agents having the capacity to treat or prevent bone injury or metabolic disorders based on their ability to promote bone formation or inhibit bone resorption.

BRIEF SUMMARY OF THE INVENTION

The present invention includes a bone-targeting compound, having an affinity for bone, for example, the extracellular inorganic matrix of the bone. Such affinity allows the bone-targeting compound to deliver agents to the bone for interaction therewith. The agents being delivered to the bone may have the capacity to diagnose, treat or prevent bone metabolic disease or injury. The present invention also includes methods for the synthesis of and methods for the use of the bone-targeting compound.

The compound of the present invention has the following formula:

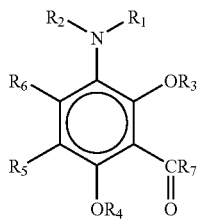

Formula I wherein $R_1$ and $R_2$ are independently hydrogen, lower alkyl, aryl lower alkyl, or aryl, $R_3$ is hydrogen or lower alkyl, $R_4$ is hydrogen, lower alkyl, aryl lower alkyl or aryl, $R_5$ and $R_6$ are independently hydrogen or lower alkyl, or $R_5$ and $R_6$ taken together with the carbon atoms to which they are attached form a ring containing up to about 10 ring carbon atoms and up to a total of about 18 carbon atoms, and $R_7$ is hydroxy, lower alkoxy or $NR_8R_9$, wherein $R_8$ and $R_9$ are independently hydrogen or lower alkyl.

As used herein, the term "lower alkyl", when used alone or in combination, refers to alkyl groups containing 1 to about 6 carbon atoms. They may be straight-chained or branched. Examples include methyl, ethyl, propyl, isopropyl, n-butyl, sec-butyl, t-butyl, isobutyl, n-pentyl, isopentyl, neopentyl, n-hexyl, and the like. In certain embodiments, the alkyl group may contain 1 to about 3 carbon atoms.

"Aryl," when used alone or in combination with other groups, refers to an aromatic group containing ring carbon atoms and having about 6 to about 14 ring carbon atoms and up to a total of about 18 ring or pendant carbon atoms. Examples include phenyl, α-naphthyl, β-naphthyl, tolyl, xylyl, and the like.

"Aryl lower alkyl" refers to an aryl group bonded to a bridging alkyl group, as defined herein. Examples include benzyl, phenethyl, naphthylethyl, and the like.

"Lower alkoxy" refers to any of the above mentioned alkyl or aryl groups linked to an oxygen atom.

Each of the aforementioned substituents could be substituted or unsubstituted. For example, "lower alkyl" may include substituted lower alkyl.

For purposes of simplicity, the agents having the capacity to diagnose, treat or prevent bone injury will be referred to hereinafter as "bone active agents." Examples of bone active agents include: Androgenic agents; Carbonic anhydrase inhibitors; Cathepsin inhibitors; DHEA (3β-hydroxyl-5-androsten-17-one); Estrogenic agents; Free radical scavengers; HMG CoA reductase inhibitors (statins); Ipriflavone; Matrix metalloproteinase inhibitors; NO generating agents (blood flow); Non-steroidal anti-inflammatory agents (NSAIDs); Proton pump inhibitors; Sex hormones, preferably in their steroid form; Vitamin D metabolites and analogs, growth factors; Autocoids; Estrogenic agents; Parathyroid hormone; and RANK-L. It is contemplated that the bone active agents that may be used with the present invention have the ability, once delivered to bone, to interact with bone and affect its metabolism, for example, by promoting bone formation, inhibiting bone resorption, or both.

The present invention is also directed to the pharmaceutical compositions containing a pharmaceutically effective amount of the compounds of Formula I with an associated bone active agent. In addition, the present invention is directed to methods for the diagnosis, treatment and prevention of bone injury by delivering bone active agents to bone, for interaction therewith, in an animal, for example, mammals, including cats, dogs, horses, rabbits, rats and humans.

DETAILED DESCRIPTION OF EXEMPLARY EMBODIMENTS OF THE INVENTION

Figure 1:
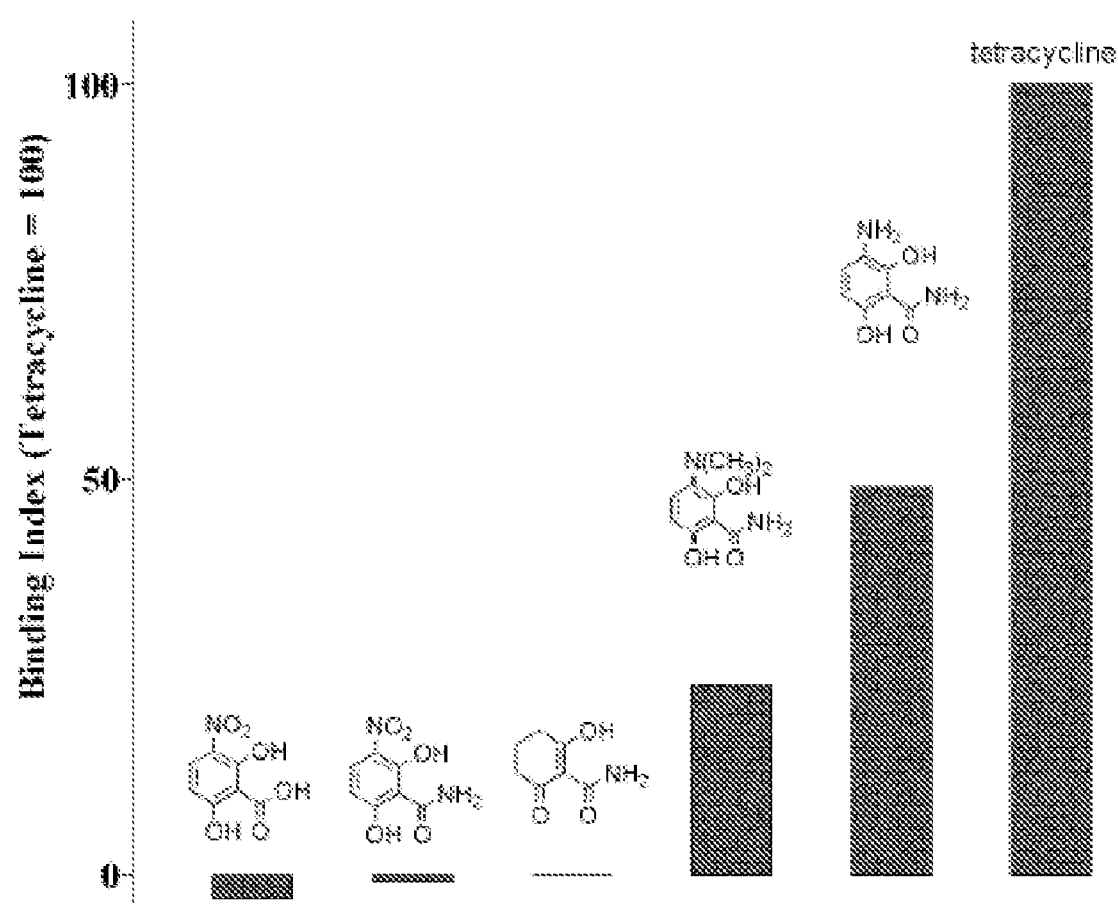
FIG. 1 is a bar graph showing the hydroxyapatite binding of exemplary bone-targeting compounds, expressed as a percentage of tetracycline binding.

The present invention is a bone targeting compound having an affinity for the extracellular inorganic matrix of bone such that it is useful for delivering bone active agents to bone for interaction therewith.

The compound of the present invention has the following formula:

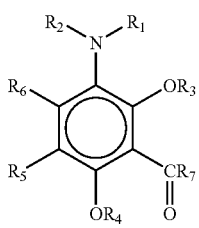

Formula I wherein $R_1$ and $R_2$ are independently hydrogen, lower alkyl, aryl lower alkyl, or aryl, $R_3$ is hydrogen or lower alkyl, $R_4$ is hydrogen, lower alkyl, aryl lower alkyl or aryl, $R_5$ and $R_6$ are independently hydrogen or lower alkyl, or $R_5$ and $R_6$ taken together with the carbon atoms to which they are attached form a ring containing up to about 10 ring carbon atoms and up to a total of about 18 carbon atoms, and $R_7$ is hydroxy, lower alkoxy or $NR_8R_9$, wherein $R_8$ and $R_9$ are independently hydrogen or lower alkyl.

For example, an embodiment of the present invention, $R_1$ may be hydrogen or lower alkyl. For another example, in certain embodiments, $R_2$ may be hydrogen. For another example, $R_3$ may be hydrogen or an alkyl group containing 1 to about 3 carbon atoms or aryl lower alkyl, such as benzyl. For another example, $R_4$, $R_5$, and $R_6$ may each be hydrogen. For another example, in an embodiment of the present invention, $R_5$ and $R_6$ taken together may form a ring containing about 6 to about 14 ring carbon atoms. This ring system may be monocyclic, bicyclic or tricyclic. In addition, the cyclic moiety may be saturated, partially unsaturated or aromatic. For another example, $R_7$ may be $NR_8R_9$, wherein $R_8$ and $R_9$ are each hydrogen.

Synthesis of the Compounds of the Present Invention

The compound of Formula I is prepared by using methods known to a person of ordinary skill in the art. For example, the compound of Formula I may be prepared as follows:

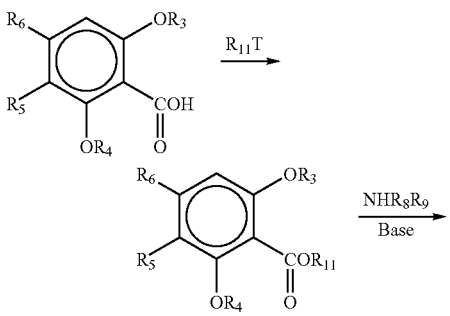

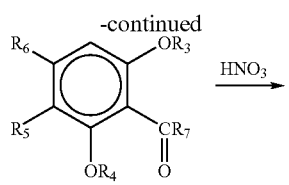

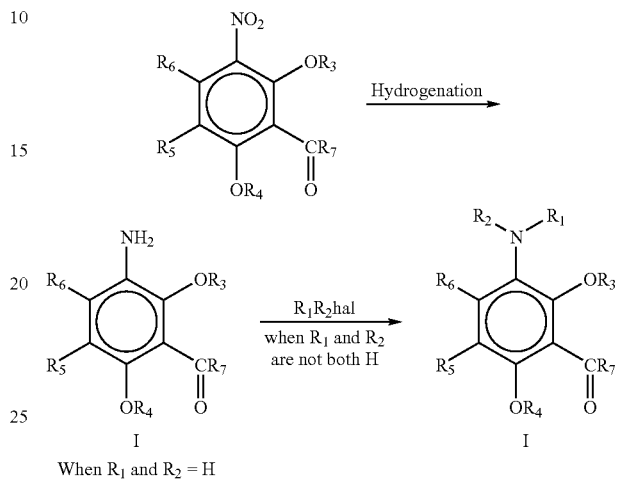

wherein $R_1$, $R_2$, $R_3$, $R_4$, $R_5$, $R_6$, $R_7$, $R_8$, $R_9$ are as defined hereinabove and $R_{11}$ is lower alkyl or aryl and hal is halide (e.g., Br, I, or Cl) and T is hal, especially bromides and iodides. The starting material for this synthesis may be obtained commercially or prepared easily from a commercially available material.

The purpose of forming the compound of

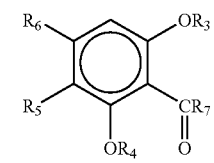 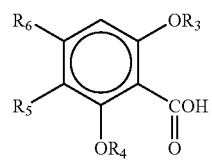

from

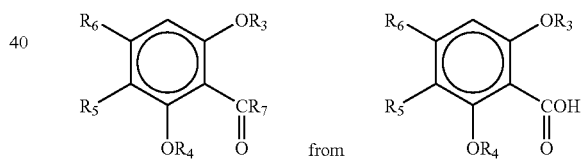

is to convert the acid functionality to the corresponding amide. If neither $R_3$ nor $R_4$ are hydrogen, then one method is to convert the acid to the corresponding acyl halides utilizing halogenating reagents, such as thionyl chloride, $PZ_3$, $PZ_5$, (wherein Z is Cl or Br), $Ph_3P$ in $CCl_4$, cyanuric fluoride, and the like, and the acid chloride is reacted with $NHR_8R_9$ to form the corresponding amide.

However, if $R_3$ or $R_4$ are hydrogen, the hydroxy group is reactive with many of these reagents, e.g., $SOCl_2$, $PZ_3$ and $PZ_5$, and this route cannot be taken. In this case, the hydroxy group may be protected using protecting groups described in "PROTECTIVE GROUPS IN ORGANIC SYNTHESIS" by T. W. Greene, John Willey & Sons, Inc., N.Y., 1981, ("Greene"), the contents of which are incorporated by reference, such as converting the alcohol to methoxymethyl (MOM) or 2-methoxyethoxymethyl (MEM).

Alternatively, the acid functionality is converted to an ester under Fischer esterification conditions, which is then reacted with the amine to form the amide. In the method illustrated, the carboxylic acid,

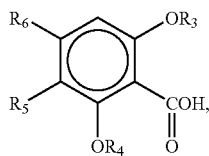

is reacted with a base, such as hydroxide and then the corresponding salt is reacted with an alkyl halide ($R_{11}T$), such as a bromide or an iodide, to form the corresponding ester, which in turn is reacted with the amine $NHR_8R_9$ in base (such as, hydroxide) to form in the corresponding amide, which is

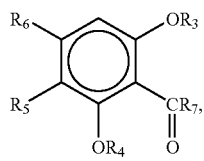

in the illustrated example. This product in turn is reacted with nitric acid to form the corresponding nitro compound,

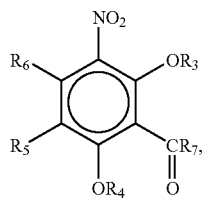

which is reduced by reducing agents known in the art, such as Zn, Sn or Fe and acid, and Pd/C and the like to form the primary amine, (i.e., the compound of Formula I when $R_1$ and $R_2$ are both hydrogen. This product in turn may be reacted with $R_1R_2$hal, if an alkylamine or dialkylamine is desired.

The bone active agent being delivered to bone by the compound of the present invention may be chemically bonded thereto. Additionally, the bone active agent may be bonded at the compound in the place of either $R_1$, $R_2$, $R_6$ or $R_7$.

As described hereinabove, the compound of the present invention is characterized by its bone seeking affinity, which may be described as having the capability to bind to calcium salts with a tendency to accumulate in bone and to incorporate into its crystal lattice. The compound of the present invention has been found to exhibit bone seeking affinity.

Without wishing to be bound by theory or mechanism, it is believed that the compound of the present invention interacts with calcium in the bone in the manner illustrated below using an embodiment of the compound of the present invention:

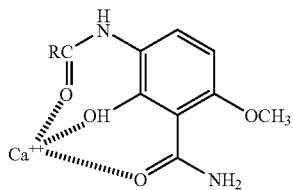

As shown by the example, three positions of the benzamide moiety interact with the calcium resulting in the compound of the present invention localizing in the bone. More specifically, the $R_2$ moiety (e.g., the OH), the acyl group of $COR_6$ moiety, and the acyl group bonded to $NHR_1$, bind to the calcium of the bone.

The compound of the present invention may contain one or more asymmetric carbon atoms and may exist in racemic and optically active forms. Depending upon the substituents, the present compounds may form additional salts as well. All of these other forms are contemplated to be within the scope of the present invention. The compound of the present invention may exist in stereoisomeric forms and the products obtained can be mixtures of the isomers.

A pharmaceutical form of the active compound may be administered in a number of manners. The compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

The tablets, troches, pills, capsules and the like may also contain the following: a binder such as gum tragacanth, acacia, corn starch or gelatin; excipients; disintegrating agents such as corn starch, potato starch, alginic acid and the like; lubricants; and a sweetening agent such as sucrose, lactose or saccharin may be added or a flavoring agent such as peppermint, oil of wintergreen, or cherry flavoring. When the dosage unit form is a capsule, it may contain, in addition to materials of the type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non toxic in the amounts employed. In addition, the active compound may be incorporated into sustained release preparations and formulations.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. The form should be sterile and fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, the inclusion of isotonic agents may be desirable, for example, sugars or sodium chloride. Prolonged absorption of the injectable compositions can be brought about by the use in the compositions of agents, delaying absorption, for example, aluminum monostearate and gelatin.

Sterile injectable solutions may be prepared by incorporating the active compound in the required amount in the appropriate solvent with various of the other ingredients enumerated above, followed by filtered sterilization. Generally, dispersions may be prepared by incorporating the various sterilized active ingredient into a sterile vehicle containing the basic dispersion medium and the required other ingredients from those enumerated above. In the case of sterile powders for the preparation of sterile injectable solutions, methods of preparation include vacuum drying and freeze drying techniques, which yield a powder of the active ingredient plus any additional desired ingredient from previously sterile filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In Vitro Testing of Bone Targeting

The ability of the compounds of the present invention to target bone is estimated by determination of the ability of the compounds to be bound to microcrystalline hydroxyapatite $[Ca_{10}(PO_4)6.OH_2]$ (HA) from a dilute aqueous solution.

Solutions of test compounds are constructed in 99:1, v/v, $H_2O$:dimethylsulfoxide (DMSO) at $10^{-5}M$.

These solutions are taken for determination of electronic photometric absorption, with spectral scanning from $\lambda=500-190$ nm. Absorption maxima $(\lambda_{max})$ and extinction coefficients ($\epsilon$) are determined using the Beer-Lambert law.

For binding determinations, 1 mL of each solution is taken and added to 0.1 mL of trishydroxymethylaminomethane (50 mM) in 1% DMSO (aq) that contained either 0 or 0.5% (w/v) of slurried HA. These solutions and slurries are mixed for 4 minutes, then centrifuged for 3 minutes at 10,000×g. Supernatants are taken for UV absorption spectrometry at previously determined $\lambda_{max}$, concentrations of test compound are determined and the extent of binding is calculated. Tetracycline is included as a positive control compound.

The compound of the present invention has been found to have a strong affinity for hydroxyapatite, similar to that of tetracycline, which is known to have a strong binding affinity to bone. For example, with reference to FIG. 1, the hydroxyanatite binding index of embodiments of the compound of the present invention are expressed as a percentage of tetracycline binding, which binding indexes illustrate the bone-seeking affinity of the compound of the present invention.

Other embodiments of the invention will be apparent to those skilled in the art from consideration of the specification and practice of the invention disclosed in this application. It is intended that the Specification be considered as exemplary only, and not intended to limit the scope and spirit of the invention.

Unless otherwise indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth are approximations that may vary depending upon the desired properties sought to be determined by the present invention.

Notwithstanding that the numerical ranges and parameters setting forth the broad scope of the invention are approximations, the numerical values set forth in the examples are reported as precisely as possible. Any numerical value, however, inherently contain certain errors necessarily resulting from the standard deviation found in their respective testing measurements.

Any publication referenced in this application is incorporated herein by reference.

What is claimed is:
1. A composition, comprising:
a compound of the formula

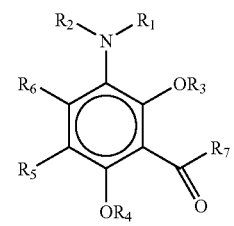

wherein
$R_1$ is hydrogen, lower alkyl, aryl lower alkyl, or aryl;
$R_2$ is hydrogen, lower alkyl, aryl lower alkyl, or aryl;
$R_3$ is hydrogen or lower alkyl;
$R_4$ is hydrogen, lower alkyl, aryl lower alkyl or aryl;
$R_5$ and $R_6$ are independently hydrogen or lower alkyl, or $R_5$ and $R_6$ taken together with the carbon atoms to which they are attached form a ring containing up to 10 ring carbon atoms and up to a total of 18 carbon atoms,
$R_7$ is hydroxy, lower alkoxy or $NR_8R_9$;
$R_8$ is hydrogen or lower alkyl; and
$R_9$ is hydrogen or lower alkyl;
wherein said compound has an affinity for bone; and
a bone active agent associated with said compound, wherein said bone active agent is selected from: cathepsin inhibitor, free radical scavenger, ipriflavone, matrix metalloproteinase inhibitor, NO-generating agent, non-steroidal anti-inflammatory agent, growth factor, autocoid, and RANK-L antagonist.

2. The composition according to claim 1 wherein $R_5$ and $R_6$ are both hydrogen.

3. The composition according to claim 1 wherein $R_7$ is $NR_8R_9$.

4. The composition according to claim 3 wherein $R_8$ and $R_9$ are both hydrogen.

5. The composition according to claim 1 wherein $R_3$ is hydrogen.

6. The composition according to claim 1 wherein
$R_1$, $R_2$, $R_3$, $R_5$ and $R_6$ are each hydrogen;
$R_4$ is lower alkyl or hydrogen; and
$R_7$ is $NH_2$.

7. The composition according to claim 6 wherein $R_4$ is hydrogen.

8. The composition according to claim 1 wherein the compound is

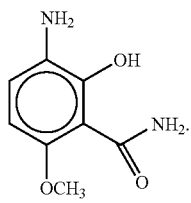

9. The composition according to claim 1 wherein the compound is

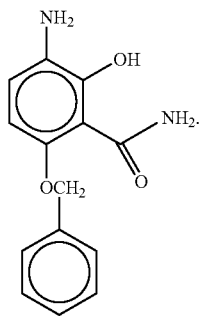

10. The composition according to claim 1 wherein $R_5$ and $R_6$ taken together with the carbon atoms to which they are attached form a ring containing between 6 and 14 ring carbon atoms, the ring being monocyclic, bicyclic or tricyclic.

11. The composition according to claim 1, wherein
$R_1$ and $R_3$ are independently hydrogen, or lower alkyl;
$R_2$, $R_4$, $R_5$ and $R_6$ are each hydrogen; and
$R_7$ is $NH_2$.

12. The composition according to claim 1, wherein
$R_1$ is hydrogen or lower alkyl;
$R_2$, $R_4$, $R_5$ and $R_6$ are each hydrogen;
$R_3$ is hydrogen or lower alkyl containing 1 to 3 carbon atoms; and
$R_7$ is $NH_2$.

13. The composition according to claim 12, wherein $R_1$ and $R_3$ are hydrogen.

14. The composition according to claim 13, wherein
$R_1$, $R_2$, $R_3$, $R_5$ and $R_6$ are each hydrogen;
$R_4$, $R_8$, and $R_9$ are independently hydrogen or lower alkyl; and
$R_7$ is $NR_8R_9$.

15. The composition according to claim 1, wherein said bone active agent is chemically bonded to said compound.

16. The composition of claim 15, wherein said bone active agent is chemically bonded to said compound in the place of $R_1$, $R_2$, $R_6$, or $R_7$.

17. A pharmaceutical composition comprising a pharmaceutically effective amount of a compound according to claim 1 with an associated bone active agent according to claim 1, and a pharmaceutically acceptable carrier therefor.

18. A method for the treatment of bone disorders in an animal in need of such treatment, comprising:
providing the composition of claim 1 comprising the compound and the associated bone active agent;
allowing said compound to deliver said bone active agent to the bone of the animal; and
allowing said bone active agent to affect the metabolism of the bone.

19. The method of claim 18, wherein said bone active agent affects the metabolism of the bone by promoting bone formation, inhibiting bone resorption, or both.

20. The method of claim 18, wherein said bone active agent is chemically bonded to said compound.

21. The method of claim 20, wherein said bone active agent is chemically bonded to said compound in the place of $R_1$, $R_2$, $R_6$, or $R_7$.

22. A composition, comprising:
a compound of the formula

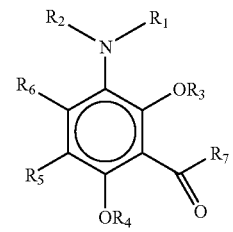

wherein
$R_1$ is hydrogen, lower alkyl, aryl lower alkyl, or aryl;
$R_2$ is hydrogen, lower alkyl, aryl lower alkyl, or aryl;
$R_3$ is hydrogen or lower alkyl;
$R_4$ is hydrogen, lower alkyl, aryl lower alkyl or aryl;
$R_5$ is hydrogen or lower alkyl;
$R_7$ is hydroxy, lower alkoxy or $NR_8R_9$;
$R_8$ is hydrogen or lower alkyl; and
$R_9$ is hydrogen or lower alkyl;
wherein said compound has an affinity for bone; and
a bone active agent is chemically bonded to said compound in the place of $R_6$.

23. The composition according to claim 22, wherein said bone active agent is selected from: cathepsin inhibitor, free radical scavenger, ipriflavone, matrix metalloproteinase inhibitor, NO-generating agent, non-steroidal anti-inflammatory agent, growth factor, autocoid, and RANK-L antagonist.

24. The composition according to claim 23, wherein at least one of $R_1$ and $R_2$ is aryl.

* * * * *